(12) United States Patent
Benz Navarrete et al.

(10) Patent No.: US 9,719,903 B2
(45) Date of Patent: Aug. 1, 2017

(54) HEAVY DYNAMIC PENETROMETER AND METHOD FOR DETERMINING THE FALL HEIGHT OF A HAMMER BELONGING TO SUCH A PENETROMETER

(71) Applicant: SOL SOLUTION, Riom (FR)

(72) Inventors: Miguel Benz Navarrete, Clermont-Ferrand (FR); Roland Gourves, Marsat (FR)

(73) Assignee: SOL SOLUTION, Riom (FR)

( * ) Notice: Subject to any disclaimer, the term of this patent is extended or adjusted under 35 U.S.C. 154(b) by 56 days.

(21) Appl. No.: 14/748,549

(22) Filed: Jun. 24, 2015

(65) Prior Publication Data
US 2016/0003724 A1    Jan. 7, 2016

(30) Foreign Application Priority Data

Jul. 4, 2014    (FR) ...................................... 14 56438

(51) Int. Cl.
*G01N 3/42*    (2006.01)
*E02D 1/02*    (2006.01)
*G01N 3/34*    (2006.01)

(52) U.S. Cl.
CPC .............. *G01N 3/42* (2013.01); *E02D 1/022* (2013.01); *G01N 3/34* (2013.01); *G01N 2203/0019* (2013.01); *G01N 2203/0039* (2013.01)

(58) Field of Classification Search
CPC .... G01N 3/42; G01N 3/34; G01N 2203/0019; G01N 2203/0039; E02D 1/022

(Continued)

(56) References Cited

U.S. PATENT DOCUMENTS 4,405,020 A * 9/1983 Rassieur ................... E21B 1/02
                                                                173/124
4,770,030 A * 9/1988 Smith ..................... E21B 25/00
                                                                73/84

(Continued)

FOREIGN PATENT DOCUMENTS

EP    0 252 863 A1    1/1988
FR    2817344 A1      5/2002

(Continued)

OTHER PUBLICATIONS

French Search Report dated Feb. 23, 2015, in corresponding French priority application.

*Primary Examiner* — Hezron E Williams
*Assistant Examiner* — Marrit Eyassu
(74) *Attorney, Agent, or Firm* — Young & Thompson

(57) ABSTRACT

The penetrometer includes a chassis, a mast mounted thereon and positioned substantially vertically during a test, a rod string, including a tip penetrating the ground that is positioned at one end of the rod string, an anvil that bears against the rod string at an end opposite the tip, a hammer striking the anvil, elements for raising the hammer along the mast up to a fall height, at which the hammer is released, and elements for measuring the sinking of the tip into the ground. The penetrometer further includes an electronic control unit for controlling the fall height, and configured to select the fall height adopted for the test based on the sinking of the tip measured by the measuring elements during one or more earlier tests, and mechanical elements controlled by the control unit for triggering the fall of the hammer at the height selected by the control unit.

9 Claims, 4 Drawing Sheets

Figure 1:
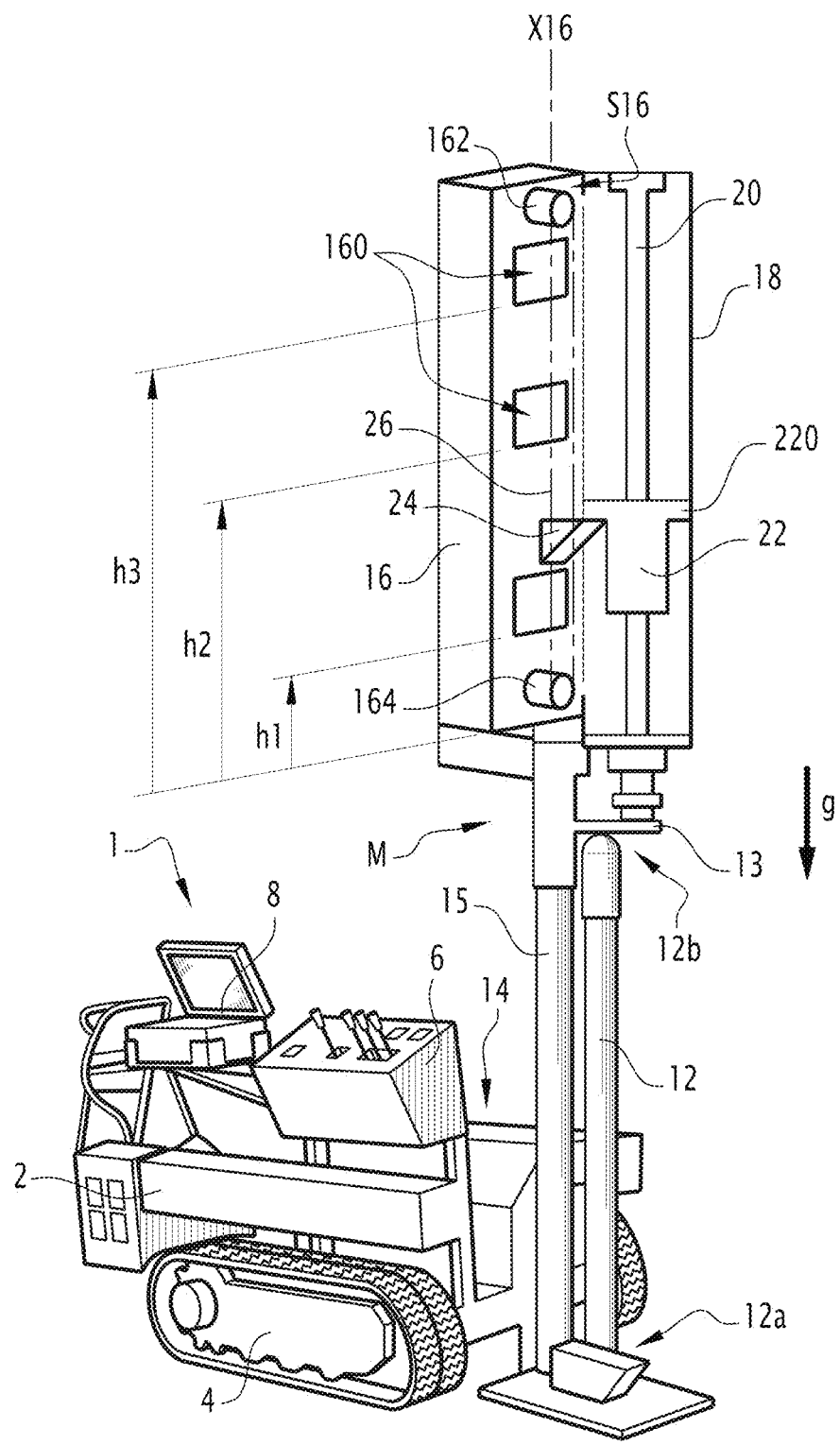

(58) Field of Classification Search
USPC .............. 73/784, 12.13, 12.01, 12.06, 78–85
See application file for complete search history.

(56) References Cited

U.S. PATENT DOCUMENTS

| | | | |
|---|---|---|---|
| 4,844,661 A | 7/1989 | Martin et al. | |
| 4,993,500 A * | 2/1991 | Greene .................. | E02D 1/025 173/1 |
| 5,607,022 A * | 3/1997 | Walker .................. | B25D 9/145 173/10 |
| 2003/0024713 A1 * | 2/2003 | Han, II .................. | E02D 1/022 173/89 |
| 2007/0131453 A1 * | 6/2007 | Yue ......................... | E02D 1/022 175/20 |
| 2015/0007640 A1 | 1/2015 | Gourves et al. | |

FOREIGN PATENT DOCUMENTS

| | | | |
|---|---|---|---|
| FR | 2822950 A1 * | 10/2002 | ............. E02D 1/022 |
| FR | 2 987 444 A1 | 8/2013 | |

\* cited by examiner

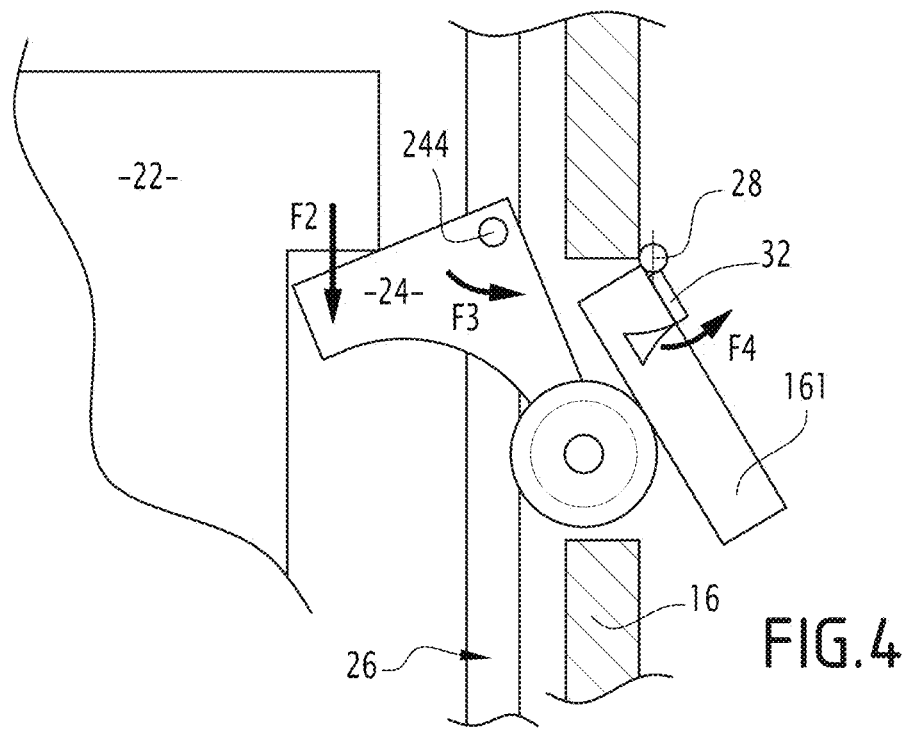
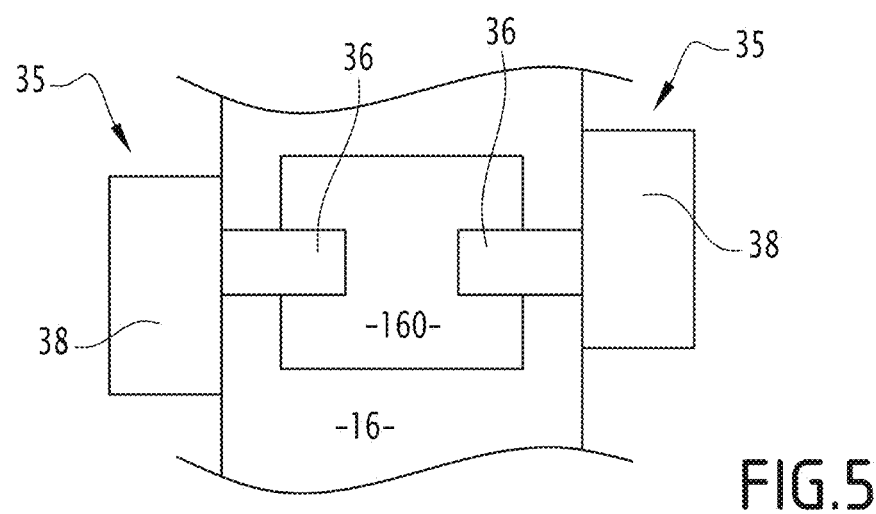

HEAVY DYNAMIC PENETROMETER AND METHOD FOR DETERMINING THE FALL HEIGHT OF A HAMMER BELONGING TO SUCH A PENETROMETER

The invention relates to a heavy dynamic penetrometer and a method for determining, during a test, the fall height to be applied to a hammer belonging to such a penetrometer based on the compactness of the soil.

Heavy dynamic penetrometers are commonly used in geotechnical reconnaissance work on the ground. More particularly, these penetrometers are generally used to measure the compactness of hard soils, such as foundation soils.

FR-A-2,987,444 in particular discloses this type of heavy dynamic penetrometer, which is marketed by the company SOL SOLUTION. This penetrometer comprises a chassis equipped with tracks for moving on the surface of the ground. A mast is mounted on the chassis. That mast is positioned vertically during a test and is generally articulated on the chassis. The penetrometer also includes a rod string, at the end of which a tip for penetrating the ground is mounted. An anvil bears against the rod string, at the end opposite the tip, and hammer is provided to strike the anvil. This hammer for example has a mass of approximately 64 kg and is released, during a test, at a constant height of approximately 75 cm, to drive the rod string into the ground. The mass is raised to its fall height using a jack and a measurement sensor is integrated into the penetrometer to measure the sinking of the tip into the soil.

Such a penetrometer is said to have a constant striking energy because the fall height and the mass of the hammer cannot be modified by the user.

The drawback of a penetrometer with a constant striking energy is that it is unable to detect layers of "soft" soil, which in particular pose problems for geotechnical engineers. Indeed, a significant quantity of energy released during the impact of the hammer on the anvil creates a very significant sinking of the tip into the ground, such that localized layers of "soft" soil are not detected during a test.

To offset this drawback, some penetrometers are equipped with a hammer with a configurable mass, i.e., the user can add or remove portions of the hammer to vary the striking energy of hammer on the anvil.

Likewise, other penetrometer models offer the possibility of varying the fall height of the hammer by adding or removing spacers above the anvil.

However, the operations consisting of manually varying the mass of the hammer or the fall height of the hammer make it necessary to stop probing, since it is in particular necessary to open the safety cage inside which the hammer slides. This results in increasing the probing time and risks injuring the operator during the operation. Furthermore, removing or adding modules with respect to the hammer to modify its mass changes the geometry of the hammer and may disrupt the measurement of the sinking of the tip into the ground. The sensors then need to be recalibrated upon each change in geometry of the hammer.

The invention more particularly aims to resolve these drawbacks by proposing a heavy dynamic penetrometer in which the striking energy of the hammer on the anvil is adjusted automatically upon each test based on the nature of the ground being probed.

To that end, the invention relates to a heavy dynamic penetrometer, comprising a chassis, a mast mounted on the chassis and positioned substantially vertically during a test, a rod string, including a tip penetrating the ground that is positioned at one end of the rod string, an anvil that bears against the rod string at an end opposite the tip, a hammer striking the anvil, means for raising the hammer along the mast up to a fall height, at which the hammer is released, and means for measuring the sinking of the tip into the ground. According to the invention, the penetrometer further comprises an electronic control unit for controlling the fall height of the hammer, which is configured to select, from among several predetermined values, the fall height to be adopted for the test based on the sinking of the tip measured by the measuring means during one or more earlier tests, and mechanical means for triggering the fall of the hammer, which are controlled by the electronic unit so that the hammer is released at the selected height of the electronic control unit.

Owing to the invention, the fall height of the hammer may be adjusted automatically by the mechanical means for triggering the fall of the hammer, under the control of the electronic unit. Furthermore, the fall height is selected based on the sinking of the tip measured during the earlier test(s). The fall height is chosen from among several predetermined values, in order to obtain an optimal sinking value, or at least situated in a trust interval, i.e., in an interval for which the penetrometric test is reliable.

According to advantageous but optional aspects of the invention, such a heavy dynamic penetrometer may incorporate one or more of the following features, considered in any technically allowable combination:

- The means for raising the hammer comprise a support stop for the hammer and the mechanical triggering means comprise windows for releasing the stop, which are distributed over the height of the mast and which are respectively situated at different heights corresponding to said predetermined values, and in that the electronic unit controls the opening of the windows.
- The windows each comprise a wing articulated on the mast and in that the mechanical triggering means further comprise bolts for selectively blocking the opening of the wing of the windows, which are controlled by the electronic control unit.
- The bolts each comprise a finger translatable to selectively block the opening movement of the wing of the window.
- The bolts each comprise a spring, configured to push the finger against a surface of the wing, under the control of the electronic unit.
- The means for raising the hammer further comprise two pull chains of the stop and in that the stop is connected in a tilting manner to the chains and tilts under the weight of the hammer in an open window when it reaches the height thereof.
- The mast comprises means for automatically returning the wing of the windows to a closed position.
- The automatic return means include a tilting hinge of the wing and a return spring for returning the window to the closed position, which is wound around the hinge.
- The stop comprises rolling bearings bearing on the mast, to rise along the latter.

The invention also relates to a method for determining, during a test, the fall height of a hammer belonging to a penetrometer as previously described. According to the invention, this method comprises the following steps:

a) measuring the sinking of the tip into the ground during one or more tests for which the fall height of the hammer is constant, b) based on the sinking measured in step a), selecting a new fall height for the hammer from among the predetermined values.

Figure 2:
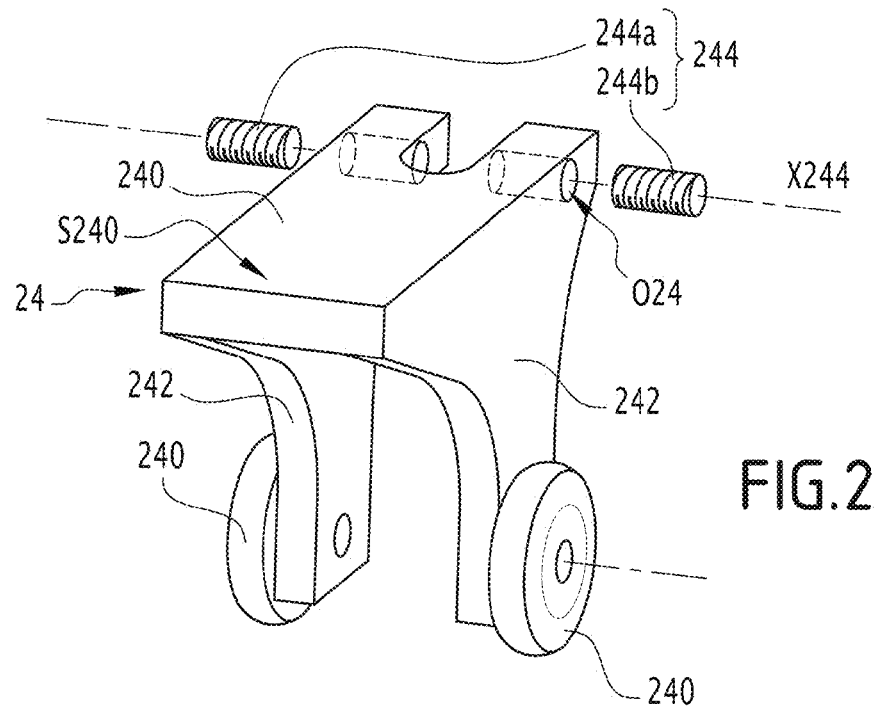
Figure 3:
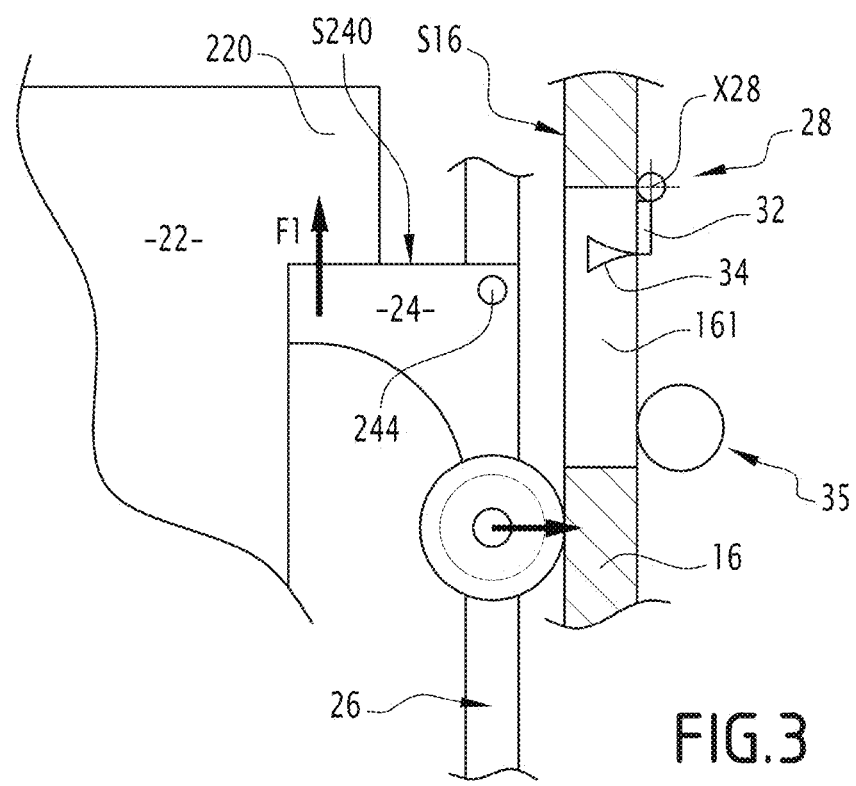
Figure 6:
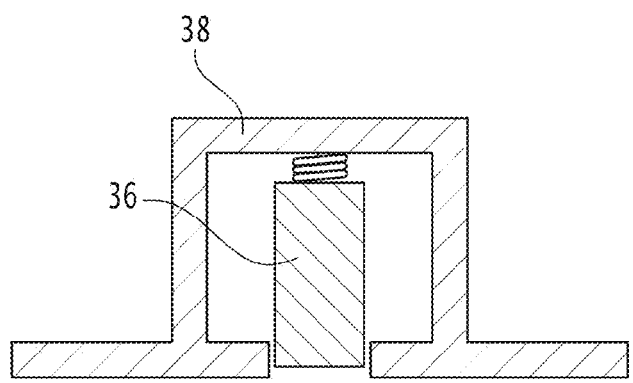
Figure 7:
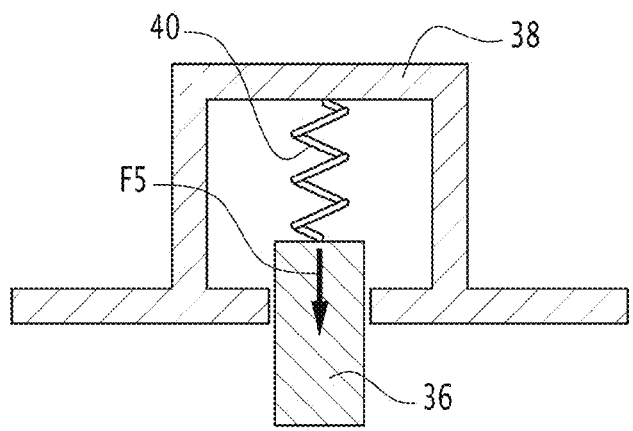
Figure 8:
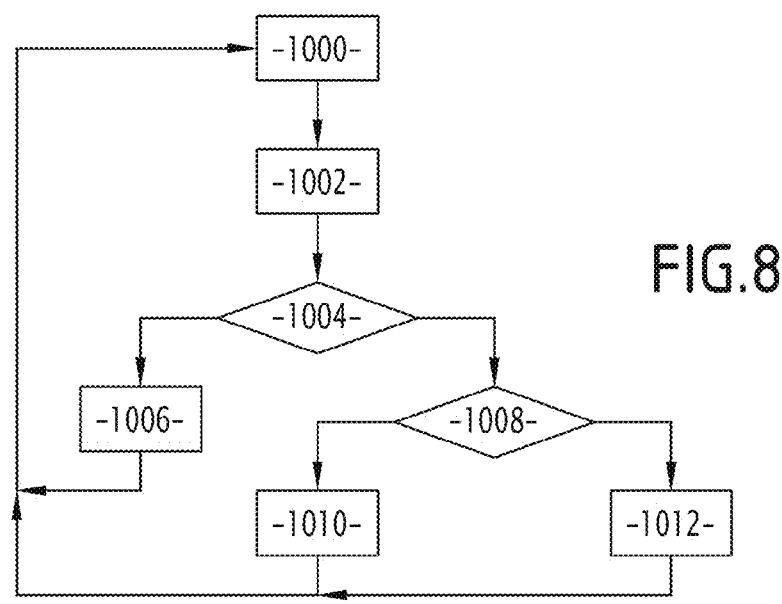

The invention and other advantages thereof will appear more clearly in light of the following description of one embodiment of a heavy dynamic penetrometer according to its principle, provided solely as an example and done in reference to the drawings, in which:

FIG. 1 is a perspective view of a heavy dynamic penetrometer according to the invention, FIG. 2 is a perspective view of a support stop of a hammer belonging to the penetrometer of FIG. 1, FIG. 3 is a partial sectional view illustrating the rise of the hammer along a mast, in which the stop supports the hammer and rolls along the mast, FIG. 4 is a sectional view similar to FIG. 3, in which the stop tilts in a window of the mast under the weight of the hammer, FIG. 5 is a partial side view of the mast, illustrating a closed window, which is blocked by bolts, FIG. 6 is a sectional view of a bolt in a retracted configuration, FIG. 7 is a view similar to FIG. 6 of a bolt in a deployed configuration, and FIG. 8 is a diagram illustrating an algorithm making it possible to determine, during a test, a fall height to be applied to the hammer.

FIG. 1 shows a heavy dynamic penetrometer 1. This penetrometer 1 comprises a chassis 2 that is equipped with tracks 4 allowing it to move on the surface of the ground. In an alternative that is not shown, the penetrometer 1 may also be installed in the trailer of a vehicle.

A mast M is articulated on the chassis 2. This mast M is positioned to be substantially vertical during a probing test. Some tests require a slight incline of the mast relative to the vertical direction. In this document, the vertical direction is defined as a direction parallel to the field of gravity g and the "top" and "bottom" directions must be interpreted relative to the vertical direction. The mast M is generally retractable and is tilted in the housing 14 of the chassis 2 when the penetrometer 1 is not in use. In this way, it is possible to fold the penetrometer 1 to place it, for example, in part of a truck or utility vehicle.

The mast M comprises a lower part 15 and an upper part 16. The upper part 16 is hollow and extends along an axis X16. It delimits several rectangular windows 160, distributed over the height of the mast. More specifically, the windows 160 are aligned in the direction of the height and are delimited on a wall S16 of the part 16. During probing, the axis X16 is substantially vertical. In the example, the part 16 of the mast M delimits three windows 160, which are respectively positioned at heights h1, h2 and h3 measured from the bottom of the part 16, parallel to the axis X16. However, as alternatives that are not shown, the part 16 may very well include two windows or more than three windows.

As shown in FIG. 3, the windows 160 each comprise a wing 161. Only one window is described below, since the windows 160 are all identical.

The wing 161 is articulated on the part 16 around a hinge 28. The hinge 28 has an axis of rotation X28 that is perpendicular to the axis X16. During a test, the axes of rotation X28 are horizontal. The wing 161 is articulated with the part 16 at an upper edge of the window 160 and the hinge 28 is positioned on an inner wall of the part 16, i.e., on the side opposite the wall S16. Thus, the tilting of the wing 161 is done toward the inside of the part 16 of the mast M.

Furthermore, the hinge 28 is connected to the wing 161 by a rivet 34 fixed in the wing, perpendicular to the thickness of the wing. That rivet 34 is connected to the hinge 28 a tongue 32 and a spring (not shown) is wound around the hinge 28, to exert elastic closing torque of the wing 161. In other words, the spring opposes the opening of the wing 161.

Furthermore, two bolts 35 are provided at each window 160 to block the opening movement of the wing 161. As shown in FIG. 5, these two bolts are each positioned on the side wall of the part 16, i.e., on a wall sharing its largest edge with that of the wall S16. In the blocked configuration, the bolts 35 oppose the rotation of the wing 161, and in the unblocked configuration, the bolts 35 do not oppose the rotation of the wing 161. As shown in FIGS. 5 to 7, the bolts 35 each include a housing 38, which is fixed on the part 16, and a finger 36 blocking the opening of the wing 161. The finger 36 of each bolt 38 is subjected to the elastic load action of a spring 40. The part 16 is provided with passage openings for the fingers 36. In the blocked configuration of the bolts 35, the fingers 36 are deployed to the openings of the part 16 inside the latter to come into contact with the inner surface of the wing 161. The fingers 36 then form an obstacle to the tilting of the wing 161 of the window 160.

The penetrometer 1 also comprises a rod string 12 that is housed in a protective shell. This rod string 12 comprises several rods, or rectilinear bars, that are arranged axially with respect to one another, parallel to the mast M. The rod string 12 comprises, at a lower end 12a, a conical tip for penetrating the ground. This tip is not shown in FIG. 1. An upper end 12b of the rod string 12 forms a striking head, which is positioned below an anvil 13 in the test configuration.

A hammer 22 is provided to fall on the anvil 13 so as to transmit striking energy to the rod string 12 by means of the striking. This striking energy is proportional to the mass and the fall height of the hammer 22. The hammer 22 is raised by a stop 24, which bears on an upper crown 220 of the hammer 22. In practice, the hammer 22 has a mass equal to 63.5 kg. The hammer 22 is movable around and along a guide part 20, which is substantially vertical during use. The movement of the hammer 22 occurs in a safety cage 18.

The stop 24 is translated in a vertical direction using a system of pulleys comprising two chains 26, a drive pulley 162, which is positioned in the upper part of the mast 16, and a driven pulley 164, which is positioned in the lower part of the mast 16. For the clarity of the drawing, the two chains are shown symbolically by a broken line in FIG. 1. The two chains 26 extend parallel to one another between the drive pulley 162 and driven pulley 164. The stop 24 is moved by the chains 26 along the surface S16.

As shown in FIG. 2, the stop 24 comprises an upper base 240 having an upper surface S240 for supporting the hammer 22. In practice, the surface S240 is in contact with a lower surface of the crown 220 of the hammer 22. The stop 24 comprises two walls 242 that extend downward from the base 240, perpendicular to the latter. These two walls 242 are parallel to one another and are each provided with a rolling bearings 240 to roll in contact with the surface S16 of the part 16. The rolling bearings 240 are preferably ball bearings. The stop 24 is attached to the chains 26 by means of two shaft ends 244a and 244b, which are each inserted into a side housing O24 of the stop 24. The shaft ends 244a and 244b are on the one hand immobilized in the housings O24, and on the other hand are each inserted into an eyelet of a chain 26. For example, the shaft ends 244a and 244b can be screwed into tappings of the stop 24, positioned similarly to the housings O24.

Furthermore, the shaft ends 244a and 244b together form a shaft 244 for tilting the stop 24 relative to the chains 26. An axis X244 is defined for the tilting of the stop 24 around the shaft 244. The axis X244 is a horizontal axis in the test configuration of the penetrometer 1, which is parallel to the tilting axes X28 of the wings 161 of the windows 160.

The penetrometer also comprises an electronic control unit 6, in the form of a console mounted on the chassis 2. The control console 6 is equipped with several actuating levers and buttons, allowing the user to activate the different functionalities of the penetrometer 1 manually. In particular, the user can control the tilting of the mast 16 or the rise of the hammer 22 using the console 6. Furthermore, the control unit 6 includes a computer, which, during each test, solves an algorithm to determine an appropriate fall height based on the nature of the ground being probed. This algorithm is explained in more detail below.

Furthermore, the penetrometer 1 is also equipped with means for measuring the sinking of the rod string 12 into the ground. These measuring means for example include an optical sensor (not shown in the figures), which is described in FR-A-2,817,344. This optical sensor is supported by the chassis 2. It is placed on the ground during a test and measures the sinking of the rod string 12 by detecting the passage of optical references marked on the surface of each of the rods of the rod string 12. These measuring means are able to communicate, after each test, the sinking value of the rod string 12 to the electronic control unit 6. For example, the transmission of the sinking value to the unit 6 can be done over a wired connection.

Lastly, the penetrometer 1 comprises a module 8 for collecting and processing signals collected by the sensor. This module 8 is an acquisition case, which is mounted on the chassis 2 in order to facilitate the reading of the results by the operator. Thus, the sensor measuring the sinking communicates both with the collection module 8 and the control unit 6.

During a test, the hammer 22 is raised upward by the chains 26, as shown by arrow F1 in FIG. 3.

As shown in FIG. 4, when the stop 24 arrives at the same axial level as an open window, i.e., a window whereof the wing 161 is free to tilt, the stop 24 tilts in a direction F3 around the shaft 244 under the weight F2 of the hammer 22. The stop 24 then drives the opening of the window 160 by tilting F4 of the wing 161 around the hinge 28. In other words, the stop 24 partially enters the window 160 and the window forms a release window stop 24. The release of the stop 24 causes the hammer 22 to fall, since the latter is no longer supported by the stop 24.

The fall height of the hammer 22 therefore corresponds to the height of the open window, i.e., the window for which the bolts 35 are in the unblocked configuration. Thus, three different fall heights for the hammer 22 are possible for the penetrometer 1. The striking energy can therefore be adapted by varying the fall height of the hammer 22.

The control unit 6 automatically manages the opening of the windows 160, by commanding the bolts 35. More specifically, the control unit 6 acts on the relaxation of the springs 40, to deploy, or not deploy, the fingers 36 and block or unblock the opening of the windows 160. In this way, the electronic unit 6 can change the fall height of the hammer 22.

The selective control of the blocking of the bolts 35 of each window 160 therefore makes it possible to precisely select the height for which the hammer 22 will be released. The bolts 35 and the windows 160 therefore form mechanical means for triggering the fall of the hammer 22, those means being controlled by the electronic control unit 6. In practice, the bolts 35 of a single window 160 from among the windows of the mast M are unblocked.

When the hammer 22 is released, the wing 161 of the window returns to the closed position by elastic return of the spring wound on the hinge 28 and the closing movement of the wing 161 drives the tilting or straightening of the stop 24. The spring wound on the hinge 28 and the latter part therefore form automatic return means for returning the wing 161 of the windows 160 to the closed position.

During a test, the fall height of the hammer 22, i.e., the striking energy provided to the rod string 12, is determined using the method described below.

When probing the ground, the first test done with the penetrometer 1 is a test done with a nominal striking energy, i.e., the hammer 22 is released at a predetermined nominal height, for example the height h2. This first test is shown by a step 1000 in FIG. 8. More generally, step 1000 represents the performance of a penetrometric test, i.e., not only the first test but also the following tests. The means for measuring sinking then read, during step 1002, the sinking value of the tip of the rod string 12 into the ground during the test.

The penetrometric tests are considered to be reliable when the sinking value of the rod string 12 into the ground is comprised in a certain interval, in particular between 2 mm and 20 mm. It therefore involves a target or trust interval. In this way, the test performed makes it possible to obtain very localized information on the structure, or the stratification, of the ground, and in particular makes it possible to detect the so-called "soft" layers, or layers with no compactness.

The control unit 6 recovers, from the collection module 8 or the sinking sensor, the sinking value of the rod string 12 into the ground in the previous test and, during step 1004, compares that value with the upper bound of the interval, which is for example 20 mm. If the sinking is greater than 20 mm, the control unit 6 then computes, during step 1006, a new fall height for the hammer 22. More specifically, this new fall height corresponds to a height below the nominal height, in particular the closest height. In other words, this new height corresponds to the height of the window situated directly below the window used to release the stop at the nominal height. In the example, starting from a nominal height h2, the fall height computed by the control unit 6 for the following test is the height h1.

However, if the sinking value of the tip in the previous test is less than 20 mm, the control unit 6 performs an additional comparison 1008, consisting of comparing the measured value with the lower bound of the interval, which is for example 3 mm. If the measured value is greater than 2 mm, the fall height adopted during the previous tests is good, since it is situated in the target interval, and the fall height is not modified for the following test.

However, if the sinking value is less than 2 mm, the striking energy is insufficient. Thus, the control unit 6 computes, during a step 1010, a new fall height for the hammer 22. This new fall height is greater than the nominal height, and corresponds to the height of the window positioned above the window used to drop the hammer 22 at the nominal height. In the example, the height goes from the nominal height h2 to the height h3.

Lastly, the new height selected during step 1006, 1010 or 1012 is used to conduct the following test, as shown by the return of the arrows connecting steps 1006, 1010 and 1012 to step 1000, which corresponds to the performance of a test. More specifically, the electronic unit 6 sends a setpoint signal to each bolt 35 to open the corresponding window at the selected for height during step 1006, 1010 or 1012.

In the following test, the sinking value considered for the selection of a new fall height will be the sinking value obtained with the adjusted height, i.e., the method is iterative.

This algorithm for calculating the fall height of the hammer 22 is resolved by the computer integrated into the unit 6 upon each impact and makes it possible to obtain a rapid convergence of the sinking value of the tip in the targeted interval. Thus, the majority of the tests result in a sinking value comprised in the target interval, and the fall height of the hammer is adapted based on the properties of the probed ground. In this way, the operator is sure that the tests conducted reflect the actual stratification of the ground, i.e., the layers of "soft" ground, or ground with a low compactness, have indeed been detected.

In an alternative that is not shown, several tests with a constant striking energy can be carried out so that the module 8 can collect a series of sinking values. This series can for example be made up of three or four values. Next, the value considered for the adjustment of the fall height of the hammer 22 in the following test can be the average, the maximum value or the minimum value of the series.

Alternatively, boundaries different from 2 mm and 20 mm for the target interval can be chosen and entered on the computer.

In an alternative that is not shown, the wing 161 of the windows 160 does not open by tilting of the stop 24, but opens directly by the control unit 6.

In an alternative that is not shown, the windows 160 are not aligned in the direction of the height, i.e., they are offset relative to one another in the horizontal direction. For example, the windows 160 can be arranged diagonally. The penetrometer then includes as many pull chains as there are windows 160, each chain supporting a stop. With this arrangement, a single chain is activated to cause the hammer to fall at the selected height.

The technical features of the alternatives and embodiments considered above may be combined to create new embodiments of the invention.

The invention claimed is:

1. A heavy dynamic penetrometer, comprising:
a chassis,
a mast, mounted on the chassis and positioned to be substantially vertical during a test,
a rod string, including a tip for penetrating the ground, which is positioned at one end of the rod string,
an anvil, which bears against the rod string, at an end opposite the tip,
a hammer for striking the anvil,
means for raising the hammer along the mast up to a fall height, at which the hammer is released,
means for measuring the sinking of the tip into the ground,
an electronic control unit for controlling the fall height of the hammer, which is configured to select, from among several predetermined values, the fall height to be adopted for the test based on the sinking of the tip measured by the measuring means during one or more earlier tests, and
mechanical triggering means for triggering the fall of the hammer, which are controlled by the electronic unit so that the hammer is released at the selected height of the electronic control unit, wherein the means for raising the hammer comprise a support element for supporting the hammer and the mechanical triggering means comprise windows for releasing the support element, which are distributed over the height of the mast and which are respectively situated at different heights corresponding to said predetermined values, and wherein the electronic unit controls the opening of the windows.

2. The dynamic penetrometer according to claim 1, wherein the windows each comprise a wing articulated on the mast and in that the mechanical triggering means further comprise bolts for selectively blocking the opening of the wing of the windows, which are controlled by the electronic control unit.

3. The dynamic penetrometer according to claim 2, wherein the bolts each comprise a finger translatable to selectively block the opening movement of the wing of the window.

4. The dynamic penetrometer according to claim 3, wherein the bolts each comprise a spring, configured to push the finger against a surface of the wing, under the control of the electronic unit.

5. The dynamic penetrometer according to claim 2, wherein the means for raising the hammer further comprise two pull chains of the support element and wherein the support element is connected in a tilting manner to the chains and tilts under the weight of the hammer in an open window when it reaches the height thereof.

6. The dynamic penetrometer according to claim 2, wherein the mast comprises automatic return means for automatically returning the wing of the windows to a closed position.

7. The dynamic penetrometer according to claim 6, wherein the automatic return means include a tilting hinge of the wing and a return spring for returning the window to the closed position, which is wound around the hinge.

8. The dynamic penetrometer according to claim 1, wherein the support element comprises rolling bearings bearing on the mast, to rise along the latter.

9. A method for determining, during a test, the fall height of a hammer belonging to a penetrometer according to claim 1, said method comprising the following steps:
a) measuring the sinking of the tip into the ground during one or more tests for which the fall height of the hammer is constant, then
b) based on the sinking measured in step a), selecting a fall height for the hammer from among the predetermined values.

* * * * *